(12) United States Patent
Hoggatt

(10) Patent No.: US 8,784,372 B1
(45) Date of Patent: Jul. 22, 2014

(54) FIRST AID PEN HAVING SEPARATE COMPARTMENTS

(76) Inventor: Johnathan D. Hoggatt, Richmond, VA (US)

(*) Notice: Subject to any disclaimer, the term of this patent is extended or adjusted under 35 U.S.C. 154(b) by 110 days.

(21) Appl. No.: 13/494,178

(22) Filed: Jun. 12, 2012

(51) Int. Cl.
*A61M 37/00* (2006.01)
(52) U.S. Cl.
USPC .............................. 604/87; 604/136
(58) Field of Classification Search
USPC ............... 604/87–89, 134–139, 195
See application file for complete search history.

(56) References Cited

U.S. PATENT DOCUMENTS

| | | | |
|---|---|---|---|
| 3,797,489 A * | 3/1974 | Sarnoff | 604/136 |
| 4,983,164 A * | 1/1991 | Hook et al. | 604/87 |
| D330,079 S | 10/1992 | Dalling et al. | |
| 6,969,370 B2 | 11/2005 | Langley et al. | |
| 8,021,335 B2 | 9/2011 | Lesch, Jr. | |
| 8,062,254 B2 | 11/2011 | MacLean | |
| 2008/0097390 A1 | 4/2008 | Dacquay et al. | |
| 2010/0137798 A1 | 6/2010 | Streit et al. | |
| 2011/0257604 A1 | 10/2011 | Banik | |

\* cited by examiner

*Primary Examiner* — Laura Bouchelle
*Assistant Examiner* — Melissa A Snyder

(57) ABSTRACT

The first aid pen having separate compartments is comprised of a pressure cap that can retract to expose a hypodermic needle suspended under and in fluid communication with a mixing chamber. The first aid pen includes a first compartment and a second compartment. The second compartment includes a membrane upon a top surface, which is punctured upon pushing a slideable member of the first compartment downwardly. Once the membrane is broken, the contents of the first compartment descends into and mix with the contents of the second compartment, and prior to intravenous or intramuscular injection via the hypodermic needle. The first compartment includes the slideable member, which is pushed downwardly in order to puncture the membrane and mix the two components stored in the respective compartment. The second compartment forms the mixing chamber when the contents of the first compartment descend therein.

7 Claims, 7 Drawing Sheets

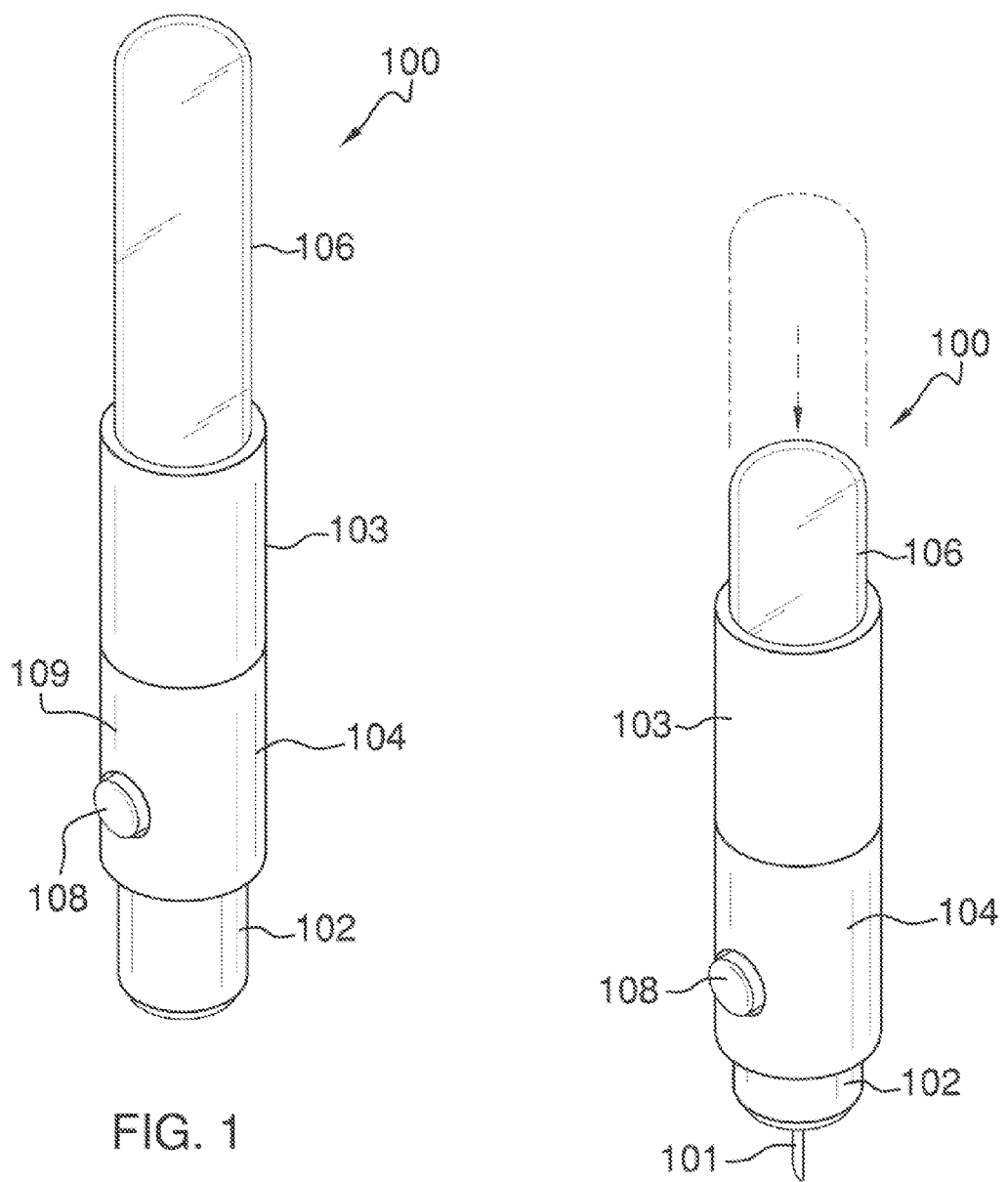

FIRST AID PEN HAVING SEPARATE COMPARTMENTS

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

A. Field of the Invention

The present invention relates to the field of first aid pens, more specifically, a first aid auto-injector pen having separate compartments that mix contents immediately prior to intravenous or intramuscular injection.

Self-service auto-injecting pens have been around for quite some time. This is especially true where the pen is directed to injection of insulin for a diabetic patient or as an epinephrine pen ("EpiPen") for injection of adrenaline for someone who is experiencing anaphylaxis due to a severe allergic reaction. These devices are life saving and provide freedom to people suffering from a plurality of different ailments.

However, the auto-injecting pens usually include a single compartment that is filled with a liquid medicine that is simply injected intravenously or intramuscularly via a hypodermic not provide the ability to inject a solution that is comprised of at least two different components, which are mixed only prior to intravenous or intramuscular injection. The ability to mix components together immediately prior to injection enables the resultant medicine to have a longer shelf life in that the two components are suspended in an inert state for an indefinite period of time, and would otherwise become less effective and expire if pre-mixed and stored in an auto-injector pen for a number of years. What is needed is an auto-injecting pen that includes multiple compartments that are sealed off from one another, and which are compromised and depleted into a mixing chamber whereby the components are able to mix together prior to injection.

The device of the present application seeks to address this need by providing an auto-injecting pen that includes multiple compartments, which mix the components stored therein prior to injection.

B. Discussion of the Prior Art

As will be discussed immediately below, no prior art discloses an auto-injector pen that includes a pressure cap that can retract to expose a hypodermic needle that is in fluid communication with a mixing chamber; wherein the auto-injector pen includes a first compartment that is situated above a second compartment, and which are sealed from one another via a membrane; whereupon puncturing of said membrane, the contents of said first compartment descend into the second compartment in order to mix the two components together prior to intravenous or intramuscular injection via the hypodermic needle; wherein the second compartment may include a powdered or dry component that constitutes the mixing chamber upon delivery of the contents of the first compartment; wherein the first compartment includes a slideable member that is pushed downwardly to puncture or otherwise break the membrane; wherein a retraction spring retracts the hypodermic needle upwardly after use as a safety measure; wherein a release button provided on an exterior surface enables the mixed contents of the mixing chamber pass into the hypodermic needle during the administration of the injection.

The Banik patent application Publication (U.S. Pub. No. 2011/0257604) discloses an additive force device for a drug delivery pen for intradermal medication injection. However, the delivery pen does not provide for multi-compartmented contents that are separated by a membrane that enables mixing prior to injection.

The Lesch, Jr. patent (U.S. Pat. No. 8,021,335) discloses a jet injector that includes a pre-filled syringe that has an injection-assisting needle and an energy source configured for biasing the plunger to produce an injecting pressure. Again, the jet injector does not provide a means for mixing two components together immediately preceding injection.

The MacLean patent (U.S. Pat. No. 8,062,254) discloses a spring-driven adjustable oral syringe. However, the syringe is not an auto-injecting pen that enables mixing of two or more components immediately prior of injection.

The Langley et al. patent (U.S. Pat. No. 6,969,370) discloses a drive mechanism for an injection device in which piston means are selectively driven to expel medicament from within a medicament cartridge. Again, no ability to mix components forming a medicine immediately preceding injection.

The Streit et al. patent application Publication (U.S. Pub. No. 2010/0137798) discloses a spring arrangement for an injection device. Again, no ability to mix components forming a medicine immediately preceding injection.

The Dacquay et al. patent application Publication U.S. Pub. No. 2008/0097390) discloses a spring actuated drug delivery system. Again, no ability to mix components forming a medicine immediately preceding injection.

While the above-described devices fulfill their respective and particular objects and requirements, they do not describe an auto-injector pen that includes a pressure cap that can retract to expose a hypodermic needle that is in fluid communication with a mixing chamber; wherein the auto-injector pen includes a first compartment that is situated above a second compartment, and which are sealed from one another via a membrane; whereupon puncturing of said membrane, the contents of said first compartment descend into the second compartment in order to mix the two components together prior to intravenous or intramuscular injection via the hypodermic needle; wherein the second compartment may include a powdered or dry component that constitutes the mixing chamber upon delivery of the contents of the first compartment; wherein the first compartment includes a slideable member that is pushed downwardly to puncture or otherwise break the membrane; wherein a retraction spring retracts the hypodermic needle upwardly after use as a safety measure; wherein a release button provided on an exterior surface enables the mixed contents of the mixing chamber pass into the hypodermic needle during the administration of the injection. In this regard, the first aid pen having separate compartments departs from the conventional concepts and designs of the prior art.

SUMMARY OF THE INVENTION

The first aid pen having separate compartments is comprised of a pressure cap that can retract to expose a hypodermic needle suspended under and in fluid communication with a mixing chamber. The first aid pen includes a first compartment and a second compartment. The second compartment includes a membrane upon a top surface, which is punctured upon pushing a slideable member of the first compartment downwardly. Once the membrane is broken, the contents of the first compartment descends into and mix with the contents of the second compartment, and prior to intravenous or intramuscular injection via the hypodermic needle. The first compartment includes the slideable member, which is pushed downwardly in order to puncture the membrane and mix the two components stored in the respective compartment. The second compartment forms the mixing chamber when the contents of the first compartment descend therein, and may require shaking of the entire assembly prior to injection. A retraction spring, shall retract the hypodermic needle upwardly after use in delivering the mixed contents as an injection.

An object of the invention is to provide an auto-injector pen that is able to mix two or more components together immediately prior to intravenous or intramuscular injection.

Another object of the invention is to provide a first compartment and a second compartment that are separated via a membrane, which is punctured in order to enable mixing of both components.

A further object of the invention is to provide a slideable member with the first compartment, which is driven downwardly in order to puncture the membrane whereby the contents of the first compartment descend into the second compartment forming the mixing chamber.

Another object of the invention is to provide separated compartments that contain liquid or powdered components that mix together upon puncturing of the membrane.

Another object of the invention is to provide a pressure cap that is spring-loaded, and which retracts upwardly when placed against a surface of the skin in order to enable the hypodermic needle to penetrate through the skin.

An even further object of the invention release button that when depressed enables the mixed contents of the mixing chamber to pass through the hypodermic needle and administer the intravenous or intramuscular injection.

Another object of the invention is to include a retraction spring that retracts the hypodermic needle upwardly after administration of the intravenous or intramuscular injection.

These together with additional objects, features and advantages of the first aid pen having separate compartments will be readily apparent to those of ordinary skill in the art upon reading the following detailed description of presently preferred, but nonetheless illustrative, embodiments of the first aid pen having separate compartments when taken in conjunction with the accompanying drawings.

In this respect, before explaining the current embodiments of the first aid pen having separate compartments in detail, it is to be understood that the first aid pen having separate compartments is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the first aid pen having separate compartments.

It is therefore important that the claims be regarded as including such equivalent construction insofar as they do not depart from the spirit and scope of the first aid pen having separate compartments. It is also to be understood that the phraseology and terminology employed herein are for purposes of description and should not be regarded as limiting.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention:

In the drawings:

FIG. 1 illustrates a perspective view of the first aid pen by itself and in a suspended state prior to use in administering a mixed medication via injection;

FIG. 2 illustrates a perspective view of the first aid pen wherein the slideable member is pushed downwardly while the pressure cap is retracted;

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 3:
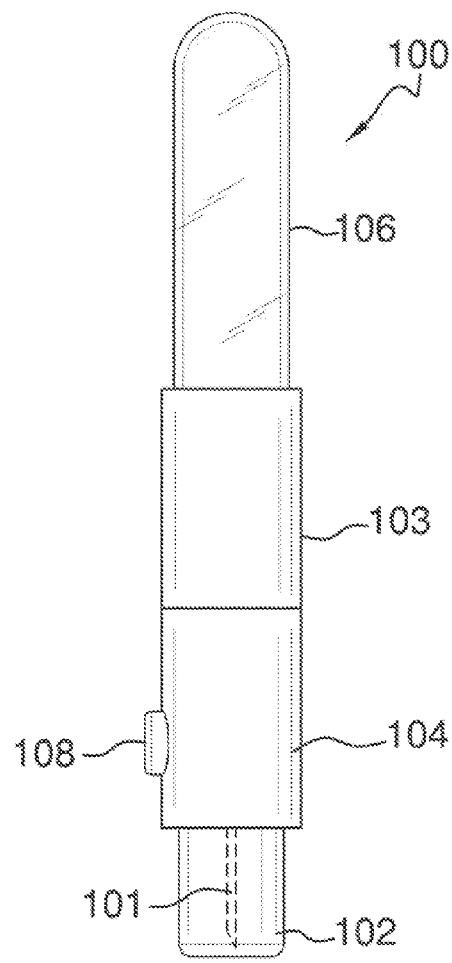
FIG. 3 illustrates a side view of the first aid pen by itself.
Figure 4:
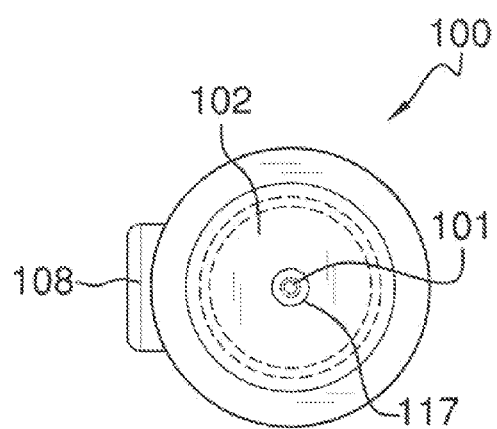
FIG. 4 illustrates a bottom view of the first aid pen.
Figure 5A:
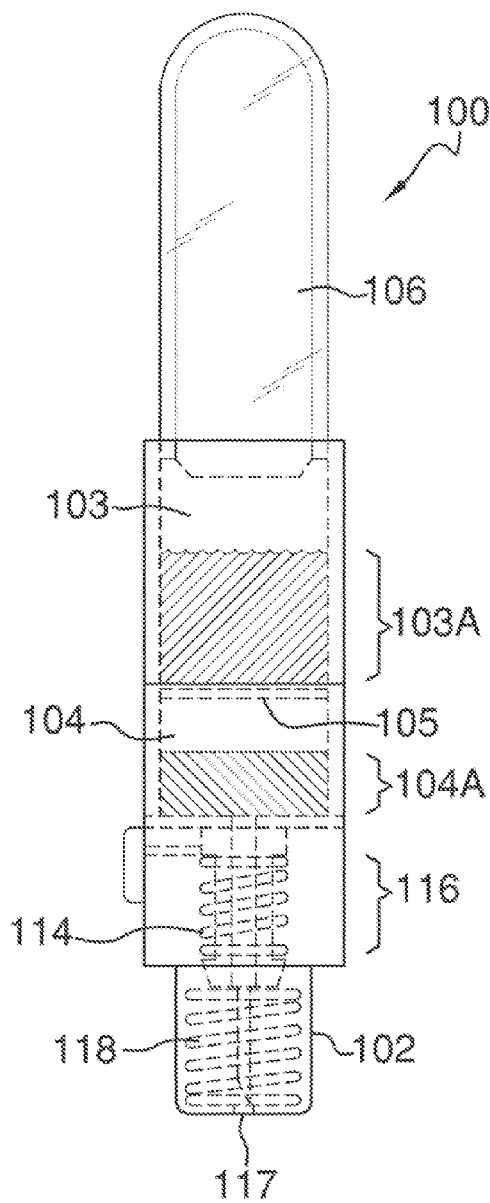
FIG. 5A illustrates a side view detailing the first compartment and second compartment separated by the membrane.
Figure 5B:
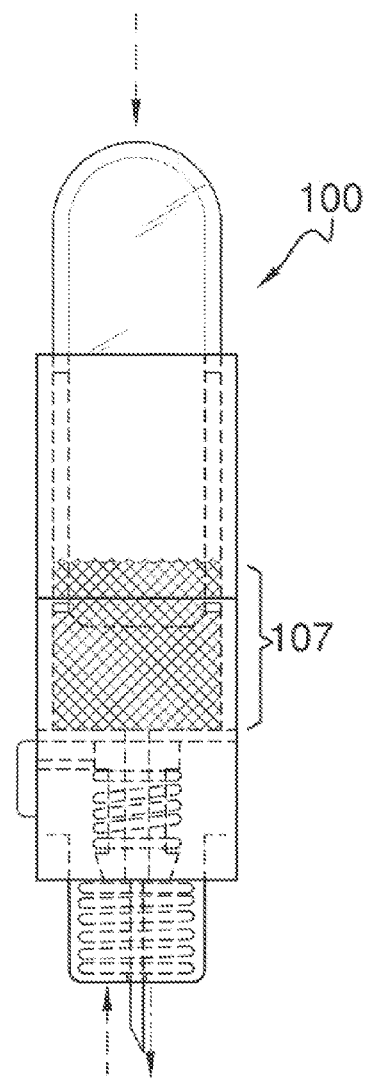
FIG. 5B illustrates a view of the slideable member pushing downwardly to puncture the membrane whilst the pressure cap is retracting upwardly exposing the bottommost end of the hypodermic needle.
Figure 6A:
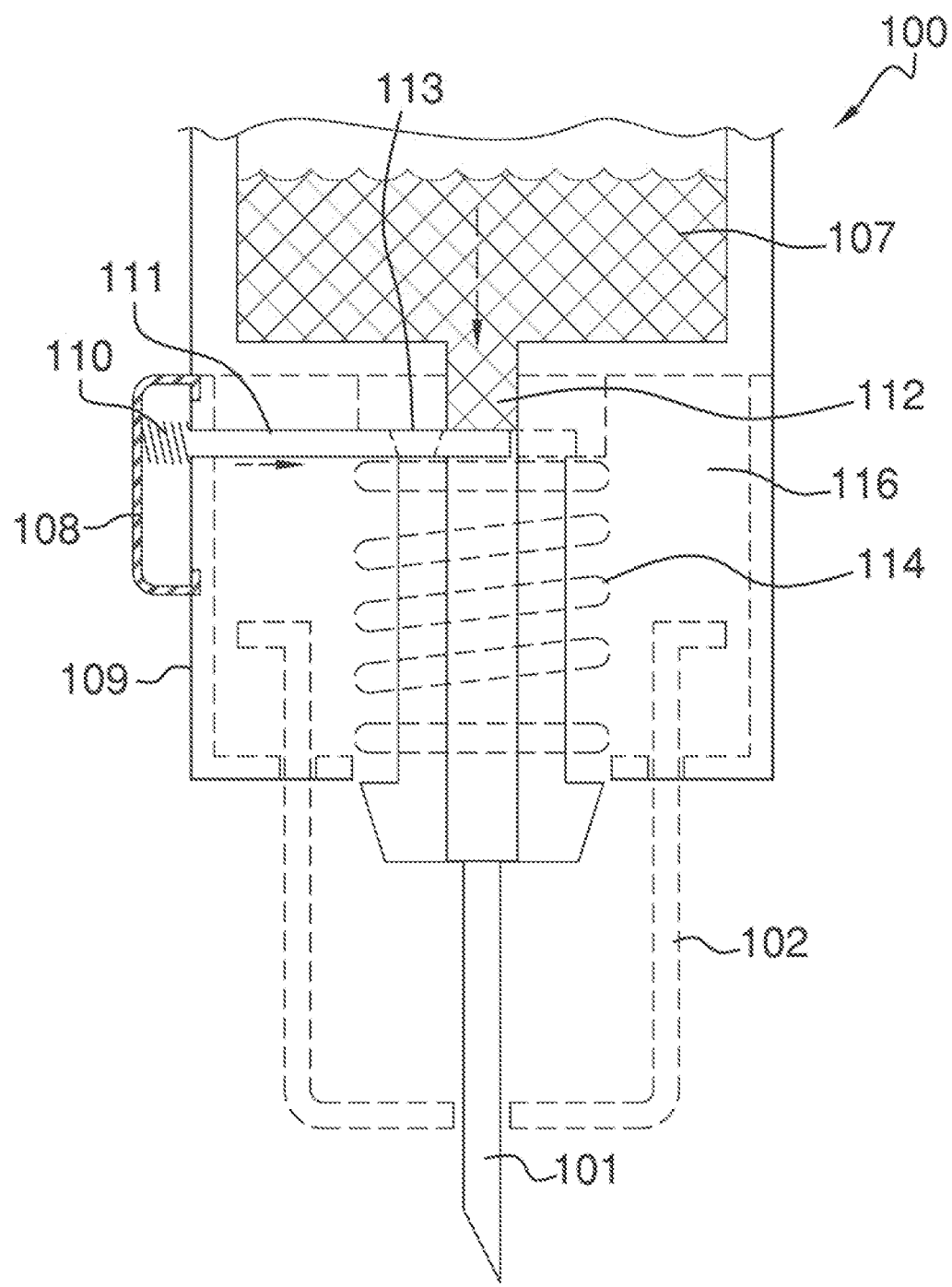
FIG. 6A illustrates a detailed view of the first aid pen wherein the pressure cap is retracted and exposing the hypodermic needle and depicting depression of the release button in order to enable uninterrupted fluid communication between the mixing chamber and hypodermic needle.
Figure 6B:
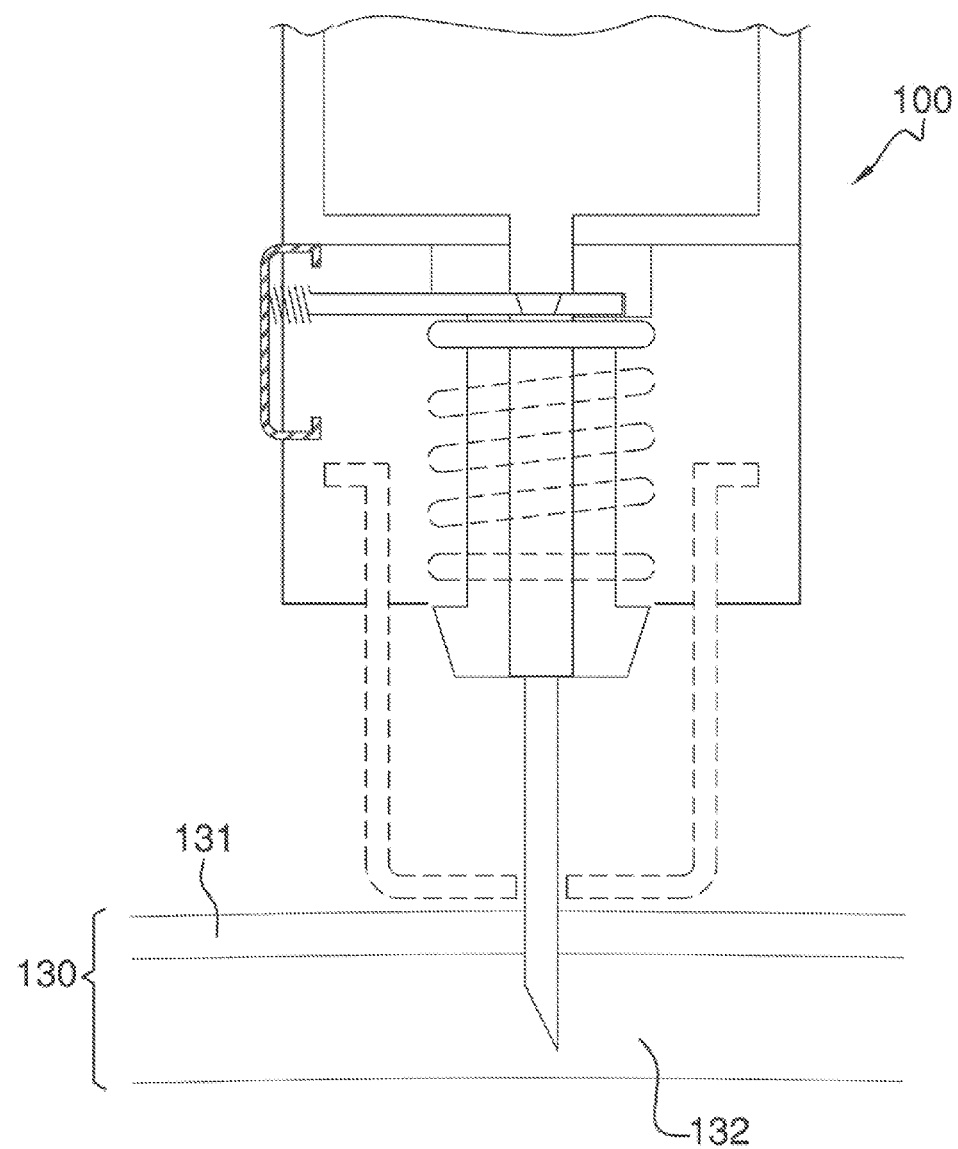
FIG. 6B illustrates a detailed view of the uninterrupted fluid communication between the mixing chamber and hypodermic needle in use administering an intravenous injection into a vein or intramuscular injection.
Figure 6C:
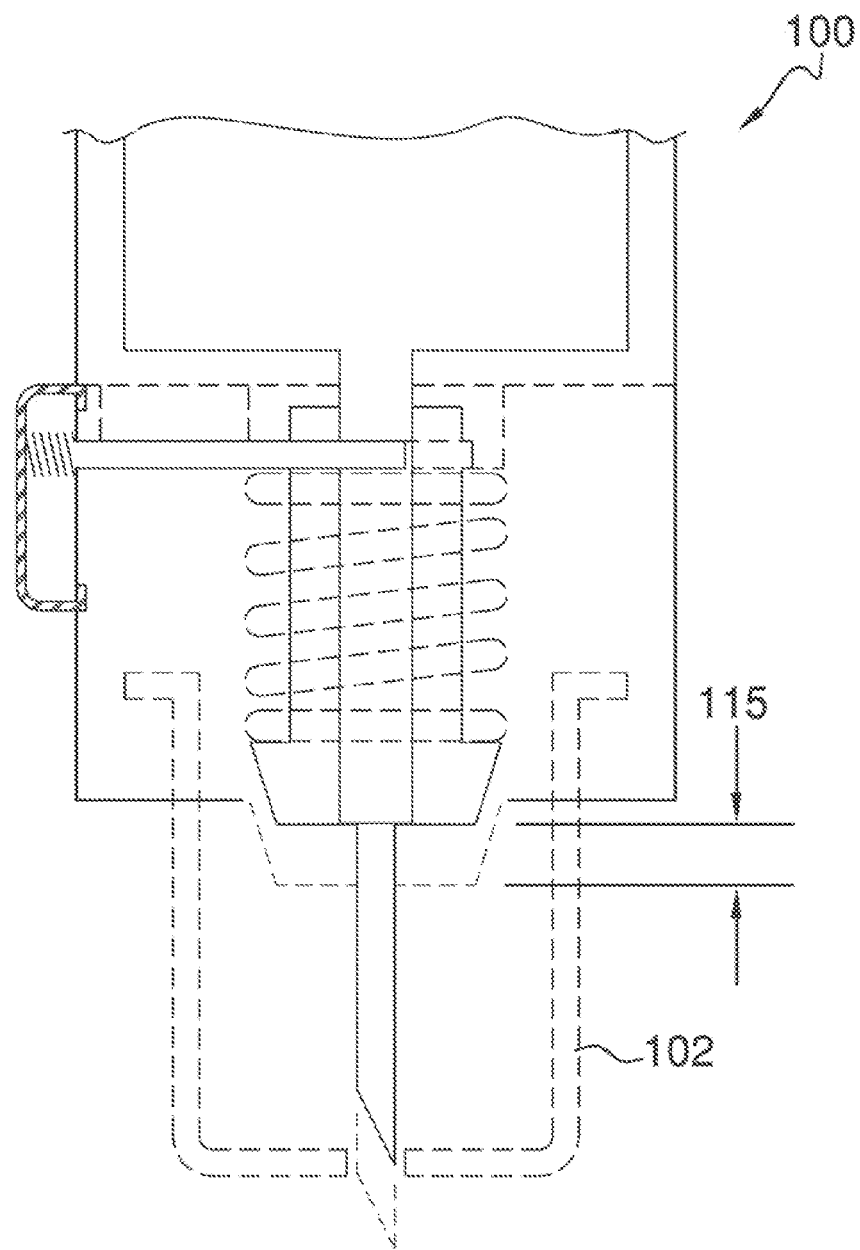
FIG. 6C illustrates a detailed view of retraction of the hypodermic needle upwardly after use in administering the injection.
Figure 6D:
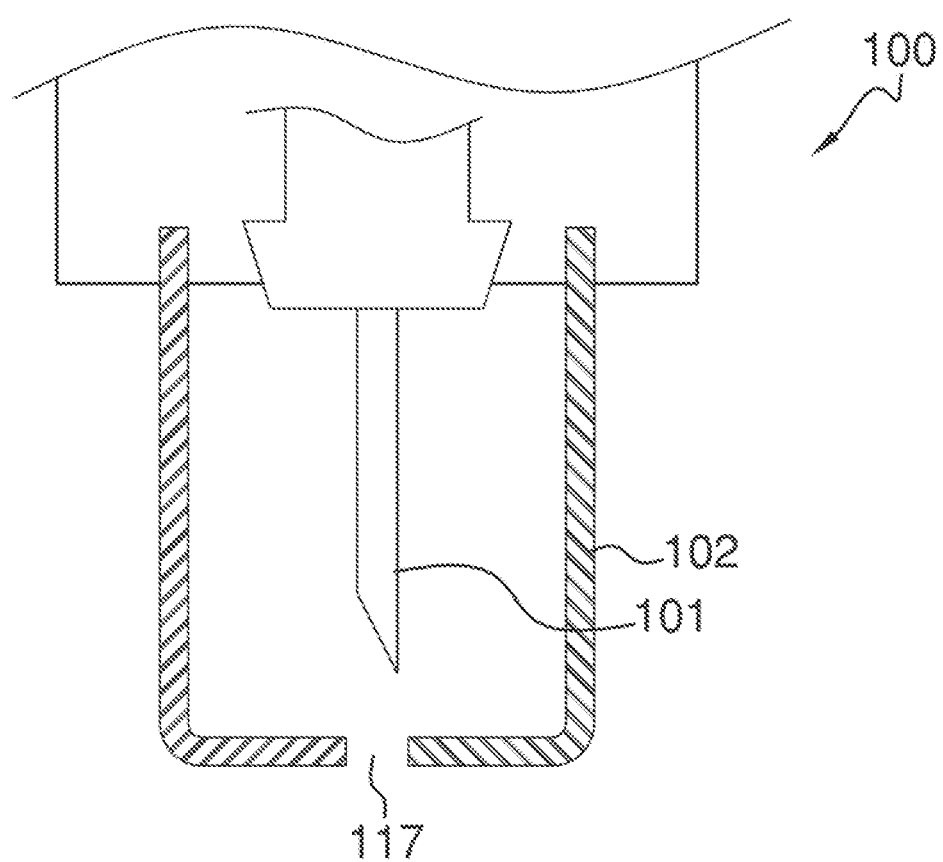
FIG. 6D illustrates a detailed view of the extension of the pressure cap downwardly with the hypodermic needle entirely concealed under the pressure cap.

Detailed reference will now be made to the preferred embodiment of the present invention, examples of which are illustrated in FIGS. 1-6D. A first aid pen having separate compartments 100 (hereinafter invention) includes a hypodermic needle 101 in slideable relation with a pressure cap 102.

The invention 100 includes a first compartment 103 and a second compartment 104 that are separated by a membrane 105. The first compartment 103 is located above and adjacent to the second compartment 104. The first compartment 103 and the second compartment 104 are able to store a liquid or powder component that when mixed shall form a medicine that is administered via the hypodermic needle 101. Moreover, the first compartment 103 shall store a first component 103A whereas the second compartment 104 shall store a second component 104A.

The membrane 105 defines the volume of the first compartment 103 and the second compartment 104 respectively. The membrane 105 may be made of a foil, plastic, latex, or other material able to punctured in order to enable fluid communication between the first compartment 103 and the second compartment 104. The first compartment 103 shall include a slideable member 106 that can slide up and down with respect to the invention 100, and when pushed downwardly (see FIGS. 2 and 5B) shall puncture and break the membrane 105 in order to enable mixing of the components of the first compartment 103 and the second compartment 104.

It shall be noted that the first component 103A of the first compartment 103 shall descend downwardly and into the second compartment 104 in order to mix together the first component 103A with the second component 104A. Moreover, the second compartment 104 alone or in conjunction with the first compartment 103 may be termed a mixing chamber upon puncture of the membrane 105. It should be noted that depending upon the particular specifications of the first component 103A and the second component 104A, it may be necessary to shake the entire invention 100 in order to produce a homogenous medicine 107.

Once the medicine 107 is properly mixed, the invention 100 is able to administer the medicine 107 as an intravenous injection. The hypodermic needle 101 is in fluid communication with the second compartment 104, and fluid flow between the second compartment 104 and the hypodermic needle 101 is governed via a release button 108 that is accessible from an exterior surface 109 of the invention 100. The release button 108 includes a button spring 110 that biases the release button 108 outwardly. Upon depression of the release button 108 a button member 111 slides across a channel 112 to align a button member hole 113 with said channel 112 thereby enabling the medicine 107 to travel down the hypodermic needle 101.

It should be noted that the depression of the release button 108 performs a second function, which is to disengage a retraction spring 114 located around the hypodermic needle 101. The retraction spring 114 is responsible for moving the hypodermic needle 101 upwardly a retraction needle distance 115 only after use of the invention 100 in administering the medicine 107 intravenously. In other words, the hypodermic needle 101 only retracts once the medicine 107 has been injected into a patient 130.

It shall be noted that the second compartment 104 is further defined by a cavity 116, which accommodates the retraction of either the hypodermic needle 101 and/or the pressure cap 102. Also, the cavity 116 accommodates the overall functionality of the components associated with the release button 108.

The pressure cap 102 is slideable engaged under the second compartment 104. Moreover, the pressure cap 102 includes a needle hole 117 that enables the hypodermic needle 101 to extend and retract with respect to the pressure cap 102. Moreover, the pressure cap 102 encompasses the entire hypodermic needle 101 except when in use administering the medicine 107 at which point the bottommost end of the hypodermic needle is exposed and used to penetrate through skin 131 in order to deliver the medicine 107 into a bloodstream 132 of the patient 130.

The pressure cap 102 includes a cap spring 118, which biases the pressure cap 102 downwardly in order to entirely encompass the hypodermic needle 101 such that upon pushing the invention 100 downwardly against the skin 131 of the patient, the hypodermic needle 101 extends through the needle hole 117 and impacts the skin 131. The cap spring 118 is located inside of the pressure cap 102, and encircles the hypodermic needle 101 so as not to obstruct the function of the hypodermic needle 101.

With respect to the above description, it is to be realized that the optimum dimensional relationship for the various components of the invention 100, to include variations in size, materials, shape, form, function, and the manner of operation, assembly and use, are deemed readily apparent and obvious to one skilled in the art, and all equivalent relationships to those illustrated in the drawings and described in the specification are intended to be encompassed by the invention 100.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A first aid pen having separate compartments comprising:
   a hypodermic needle that extends to expose a bottommost end of the hypodermic needle from a pressure cap;
   wherein a first compartment containing a first component is positioned above a second compartment containing a second component;
   wherein a member seals off the first compartment from the second compartment; wherein the first compartment includes a slideable member that when pushed downwardly engages and punctures a membrane thereby enabling the first component to descend downwardly and mix with the second component immediately prior to intravenous or intramuscular injection via the hypodermic needle;
   wherein the hypodermic needle is in fluid communication with the second compartment;
   wherein a release button controls fluid flow from the second compartment to the hypodermic needle;
   wherein the release button includes a button spring, which biases the release button outwardly, and upon depression of the release button a button member slides across a channel to align a button member hole with said channel thereby enabling uninterrupted fluid flow from the second compartment to the hypodermic needle;
   wherein a retraction spring located around the hypodermic needle when released retracts the hypodermic needle upwardly a retraction needle distance only after injection.

2. The first aid pen having separate compartments as described in claim 1 wherein the pressure cap includes a needle hole that enables the hypodermic needle to extend and retract with respect to the pressure cap.

3. The first aid pen having separate compartments as described in claim 1 wherein the pressure cap includes a cap spring, which biases the pressure cap downwardly in order to entirely encompass the hypodermic needle.

4. The first aid pen having separate compartments as described in claim 3 wherein the cap spring is located inside of the pressure cap, and encircles the hypodermic needle so as not to obstruct the function of the hypodermic needle.

5. A first aid pen having separate compartments comprising:
- a hypodermic needle that extends to expose a bottommost end of the hypodermic needle from a pressure cap;
- wherein a first compartment containing a first component is positioned above a second compartment containing a second component;
- wherein a member seals off the first compartment from the second compartment; wherein the first compartment includes a slideable member that when pushed downwardly engages and punctures a membrane thereby enabling the first component to descend downwardly and mix with the second component immediately prior to intravenous or intramuscular injection via the hypodermic needle;
- wherein the pressure cap includes a needle hole that enables the hypodermic needle to extend and retract with respect to the pressure cap;
- wherein the hypodermic needle is in fluid communication with the second compartment;
- wherein a release button controls fluid flow from the second compartment to the hypodermic needle;
- wherein the release button includes a button spring, which biases the release button outwardly, and upon depression of the release button a button member slides across a channel to align a button member hole with said channel thereby enabling uninterrupted fluid flow from the second compartment to the hypodermic needle;
- wherein a retraction spring located around the hypodermic needle when released retracts the hypodermic needle upwardly a retraction needle distance only after injection.

6. The first aid pen having separate compartments as described in claim 5 wherein the pressure cap includes a cap spring, which biases the pressure cap downwardly in order to entirely encompass the hypodermic needle.

7. The first aid pen having separate compartments as described in claim 6 wherein the cap spring is located inside of the pressure cap, and encircles the hypodermic needle so as not to obstruct the function of the hypodermic needle.

* * * * *